United States Patent
Odessky et al.

(10) Patent No.: US 9,600,934 B2
(45) Date of Patent: Mar. 21, 2017

(54) AUGMENTED-REALITY RANGE-OF-MOTION THERAPY SYSTEM AND METHOD OF OPERATION THEREOF

(75) Inventors: Adam Odessky, San Francisco, CA (US); Rashid Clark, San Francisco, CA (US)

(73) Assignee: ORANGE, Paris (FR)

( * ) Notice: Subject to any disclaimer, the term of this patent is extended or adjusted under 35 U.S.C. 154(b) by 288 days.

(21) Appl. No.: 14/129,829

(22) PCT Filed: Jun. 28, 2012

(86) PCT No.: PCT/IB2012/001441
§ 371 (c)(1),
(2), (4) Date: Aug. 19, 2014

(87) PCT Pub. No.: WO2013/001358
PCT Pub. Date: Jan. 3, 2013

(65) Prior Publication Data
US 2014/0347392 A1 Nov. 27, 2014

Related U.S. Application Data

(60) Provisional application No. 61/503,364, filed on Jun. 30, 2011.

(51) Int. Cl.
*G06T 19/00* (2011.01)
*G06T 13/40* (2011.01)
(Continued)

(52) U.S. Cl.
CPC .......... *G06T 19/006* (2013.01); *A61B 5/1121* (2013.01); *A61B 5/486* (2013.01); *G06T 13/40* (2013.01); *A61B 5/744* (2013.01)

(58) Field of Classification Search
None
See application file for complete search history.

(56) References Cited

U.S. PATENT DOCUMENTS

| | | | |
|---|---|---|---|
| 2001/0041992 A1* | 11/2001 | Lewis | G06F 19/322 705/3 |
| 2006/0247070 A1 | 11/2006 | Funk et al. | |
| 2008/0159611 A1* | 7/2008 | Tao | A61B 6/488 382/131 |

OTHER PUBLICATIONS

International Search Report and Written Opinion dated Nov. 12, 2012 for corresponding International Application No. PCT/IB2012/001441, filed Jun. 28, 2012.

(Continued)

*Primary Examiner* — Michelle Chin
(74) *Attorney, Agent, or Firm* — David D. Brush; Westman Champlin & Koehler, P.A.

(57) ABSTRACT

A server to perform a selected therapy on a user. The server may include a processor which may obtain activity information (AI) including information related to one or more of augmented-reality (AR) activity information, AR anatomical feature information, and range-of-motion (ROM) information; obtain user information including information related to one or more of the anatomy and physiology of the user; determine expected range-of-motion (EROM) information in accordance with the AI and the user information; track selected body parts (SBPs) of the user corresponding with the AR anatomical feature information; and/or render one or more augmented-reality limbs (ARLs) in relation with one or more corresponding SBPs of the user on a display of the system.

11 Claims, 6 Drawing Sheets

(51) Int. Cl.
*A61B 5/11* (2006.01)
*A61B 5/00* (2006.01)

(56) References Cited

OTHER PUBLICATIONS

Seongmin Baek et al., "Motion Retargeting and Evaluation for Vr-Based Training of Free Motions", Visual Computer Springer-Verlag Germany, vol. 19, No. 4, Jul. 2003 (Jul. 2003), pp. 222-242, XP08157850.

Merians Alma S. et al., "Virtual Reality-Augmented Rehabilitation for Patents Following Stroke", Physical Therapy Sep. 2002 LNKD-PUBMED: 12201804, vol. 82, No. 9, Sep. 2002 (Sep. 2002), pp. 898-915, XP002686889.

* cited by examiner

US 9,600,934 B2

AUGMENTED-REALITY RANGE-OF-MOTION THERAPY SYSTEM AND METHOD OF OPERATION THEREOF

CROSS-REFERENCE TO RELATED APPLICATIONS

This Application is a Section 371 National Stage Application of International Application No. PCT/IB2012/001441, filed Jun. 28, 2012, which is incorporated by reference in its entirety and published as WO 2013/001358 on Jan. 3, 2013, in English.

The present application is also based on and claims the benefit of U.S. Provisional Patent Application Ser. No. 61/503,364, filed Jun. 30, 2011, the content of which is hereby incorporated by reference in its entirety.

FIELD OF THE PRESENT SYSTEM

The present system relates to a therapy system and, more particularly, to an augmented-reality range-of-motion therapy system which determines range-of-motion of an anatomy of a user and therapy progress, and a method of operation thereof.

BACKGROUND OF THE PRESENT SYSTEM

Recently, virtual reality body-tracking systems have become popular for various applications such as video games and the like. Some system incorporated third-party body-tracking applications such as provided by Kinect™ which can be interfaced with an open source library such as OpenNI™. Accordingly, image information of a user can be captured and thereafter processed using a selected body-tracking application and data indicative of a location of the user and/or parts of the user can be returned via the open source library for further processing. Although numerous body-tracking applications exist such as those for video gaming, there is a dearth of virtual-reality body-tracking therapy systems to provide automated therapy sessions to one or more users.

SUMMARY OF THE PRESENT SYSTEM

It is an object of the present system to overcome disadvantages and/or make improvements in the prior art.

The present system provides a system, apparatus, method, and computer program portion (hereinafter each of which may be referred to as system unless the context indicates otherwise) which is configured to provide one or more augmented-reality (AR) limbs to a user, for instance for use in therapy courses, including feedback to the user.

In accordance with an aspect of the present system, there is disclosed a method of performing therapy on a user, the method including acts which are performed by processor, the method may include one or more acts of: obtaining activity information (AI) including information related to one or more of augmented-reality (AR) activity information, AR anatomical feature information, and range-of-motion (ROM) information; obtaining user information including information related to one or more of the anatomy and physiology of the user; determining expected range-of-motion (FROM) information in accordance with the AI and the user information; tracking selected body parts (SBPs) of the user corresponding with the AR anatomical feature information; and rendering one or more augmented-reality limbs (ARLs) in relation with one or more corresponding SBPs of the user.

Further, in accordance with the method, the act of rendering may include an act of animating the one or more ARLs in accordance with one or more of the AR activity information and the FROM information. Moreover, the one or more ARLs may be further linked to a corresponding SBP of one or more of the SBPs of the user. The method may further include an act of determining an actual ROM of one or more of the tracked SPBs of the user. Moreover, the method may include an act of determining a discrepancy in range-of-motion based upon a comparison of the actual ROM of the one or more tracked SBPs of the user with the corresponding FROM information. The method may also include an act of determining whether the discrepancy is greater than a threshold ROM value and rendering results of the determination.

In accordance with another aspect of the present system, there is disclosed a system to perform therapy on a user, the system may include a processor which may obtain activity information (AI) including information related to one or more of augmented-reality (AR) activity information, AR anatomical feature information, and range-of-motion (ROM) information; obtain user information including information related to one or more of the anatomy and physiology of the user; determine expected range-of-motion (FROM) information in accordance with the AI and the user information; track selected body parts (SBPs) of the user corresponding with the AR anatomical feature information; and/or render one or more augmented-reality limbs (ARLs) in relation with one or more corresponding SBPs of the user on a display of the system.

In accordance with the present system, the rendering may include animating the one or more ARLs on the display of the system in accordance with one or more of the AR activity information and the FROM information. Further, it is envisioned that the processor may link one or more of the one or more ARLs to a corresponding SBP of one or more of the SBPs of the user. Moreover, the processor may determine an actual ROM of one or more of the tracked SPBs of the user. It is further envisioned that the processor may further determine a discrepancy in range-of-motion based upon a comparison of the actual ROM of the one or more tracked SBPs of the user with the corresponding FROM information. Moreover, the processor may determine whether the discrepancy is greater than a threshold ROM value and renders results of the determination.

In accordance with yet another aspect of the present system, there is disclosed a computer program stored on a computer readable memory medium, the computer program configured to perform a therapy process on a user, the computer program including a program portion configured to obtain activity information (AI) including information related to one or more of augmented-reality (AR) activity information, AR anatomical feature information, and range-of-motion (ROM) information; obtain user information including information related to one or more of the anatomy and physiology of the user; determine expected range-of-motion (FROM) information in accordance with the AI and the user information; track selected body parts (SBPs) of the user corresponding with the AR anatomical feature information; and/or render one or more augmented-reality limbs (ARLs) in relation with one or more corresponding SBPs of the user on a display.

It is further envisioned that the program portion may be further configured to animate the one or more ARLs on the display of the system in accordance with one or more of the AR activity information and the FROM information when rendering the one or more ARLs. Moreover, the program portion may be further configured to link the one or more ARLs to a corresponding SBP of one or more of the SBPs of the user such that a portion of the one or more ARLs superimposes a portion of the corresponding SBP of the one or more SBPs. Further, it is envisioned that the program portion may be further configured to determine an actual ROM of one or more of the tracked SPBs of the user. Moreover, the program portion may also be configured to determine a discrepancy in range-of-motion based upon a comparison of the actual ROM of the one or more tracked SBPs of the user with the corresponding FROM information. Further, the program portion may be configured to determine whether the discrepancy is greater than a threshold ROM value and render results of the determination.

BRIEF DESCRIPTION OF THE DRAWINGS

The invention is explained in further detail, and by way of example, with reference to the accompanying drawings wherein.

DETAILED DESCRIPTION OF THE PRESENT SYSTEM

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well-known devices, circuits, tools, techniques, and methods are omitted so as not to obscure the description of the present system. It should be expressly understood that the drawings are included for illustrative purposes and do not represent the scope of the present system. In the accompanying drawings, like reference numbers in different drawings may designate similar elements.

The term rendering and formatives thereof as utilized herein refer to providing content, such as digital media which may include, for example, therapy sessions, results of the therapy sessions, image information, information generated and/or accessed by the present system, menu selections, menu items, messages, status information, settings, audio information, audiovisual information, etc., such that it may be perceived by at least one user sense, such as a sense of sight and/or a sense of hearing. For example, the present system may render a user interface (UI) on a display device so that it may be seen and interacted with by a user.

Further, for the sake of clarity as used herein, the term medical records (MRs) will refer to various information related to a user such as electronic medical records (EMR), personal health records (PHR), electronic health records (EHR), therapy records, medical records, psychological records, physiological records, and/or other information related to a professional care (e.g., a medical provider's care, a therapists care, a chiropractor's care, etc.), therapeutic care, etc., of a corresponding user or patient (generally patient for the sake of clarity).

Figure 1:
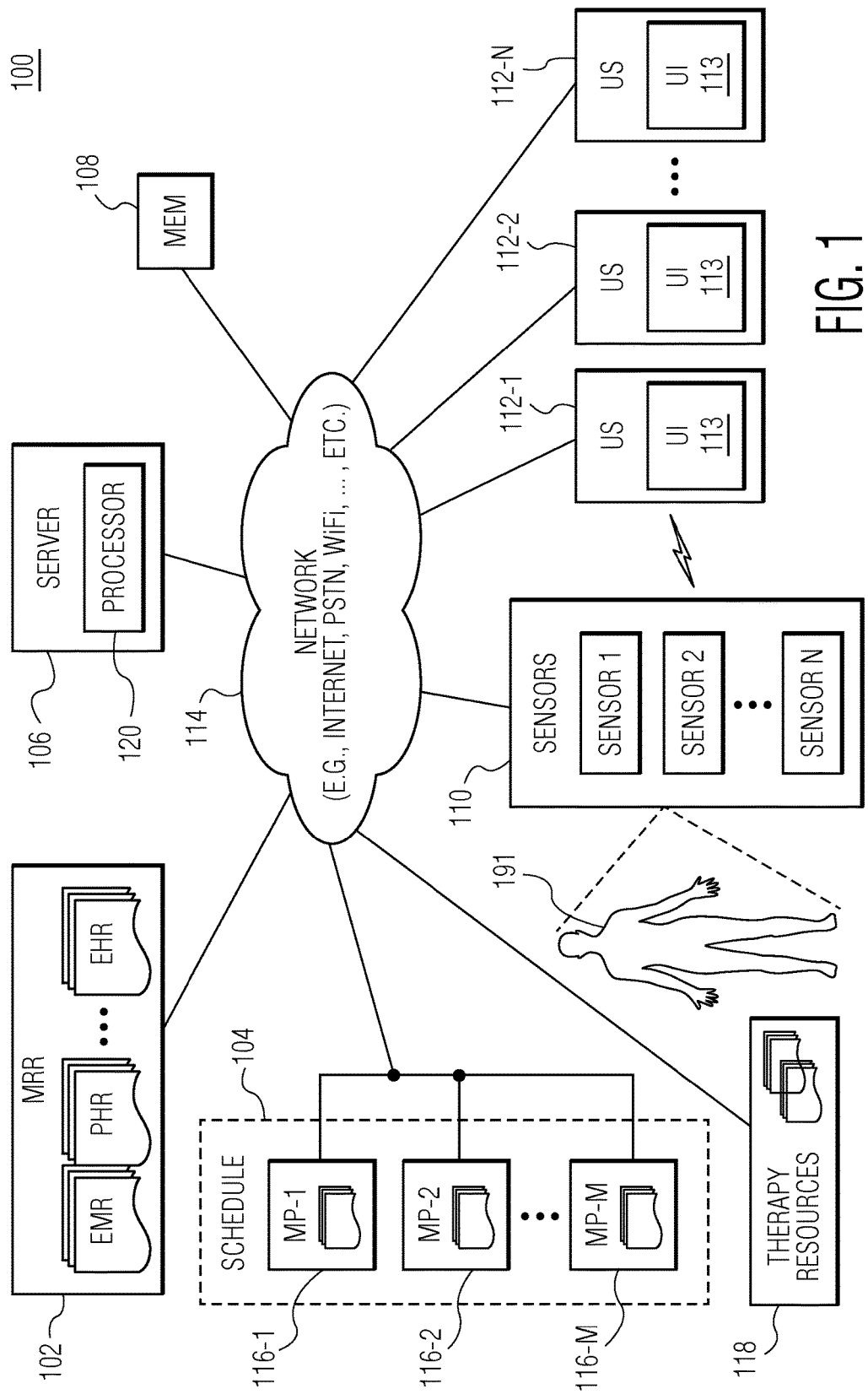
FIG. 1 is a schematic view of an AR system in accordance with embodiments of the present system.

FIG. 1 is a schematic view of an augmented-reality (AR) system 100 in accordance with embodiments of the present system. The AR system 100 may include one or more of medical record resources (MRR) 102 (e.g., a source of medical records (MRs) associated with one or more patients), schedule resources 104, a server 106, a memory 108, sensors 110, one or more user stations (US) 112-x, and therapy resources 118.

The server 106 may include a one or more processors 120 which may be situated locally and/or remotely from each other and may control the overall operation of the system 100. Accordingly, the server 106 may communicate with one or more of the MRR 102, the schedule resources 104, the memory 108, sensors 110, one or more of the US 112-x, and the therapy resources 118, to transmit and/or receive information. For example, the server 106 may request sensor information from one or more of the sensors 110, may request medical records associated with a user from the MRR 102, may request user inputs from an UI 112-x, etc. Further, the server 106 may store information (e.g., MR information, schedules, user information, account information, results of therapy sessions, etc.) which it receives and/or generates, in a memory of the system such as the memory 108 for further use. Operations performed by the processor 120 may be performed using one or more processors, logic devices, or the like, which may be locally and/or remotely located relative to each other. For example, one or more processes performed by the processor 120 (e.g., as programmed by one or more program portions stored in the memory 108) may be performed using one or more processor within, for example, one or more of the US 112-x, the sensors 110, etc.

The network 114 may include one or more networks and may enable communication between or more of the MRR 102, the schedule resources 104, the server 106, the memory 108, the sensors 110, the one or more USs 112-x, and the therapy resources 118, using any suitable transmission scheme such as wired and/or wireless communication schemes. Accordingly, the network 114 may include one or more networks such as a wide area network (WAN), a local area network (LAN), the Internet, a telephony network, (e.g., a public switched telephone network (PSTN), a 3G network, a 4G network, a 5G network, a code division multiple access (CDMA) network, a global service for mobile (GSM) network, a plain old telephone service (POTs) network, etc.), a peer-to-peer (P2P) network, a wireless fidelity (Wi-Fi™) network, a Bluetooth™ network, a proprietary network, and or other communication networks.

The memory 108 may include any suitable device in which various information of the system 100 may be stored. Accordingly, the memory 108 may include a non-transitory memory which may store information generated by the system 100 such as information related to therapies, medical treatments, medical symptoms, medical conditions, user information, professional information, schedules, operating programs, applications, settings, history, and/or other information of the system 100. The memory 108 may include portions (e.g., transitory and non-transitory) which are located locally and/or remotely from each other. Accordingly, the memory 108 may include a distributed memory such as a surface area network (SAN) or the like. Moreover, the memory 108 may be accessible via a local connection or remotely over a network such as the network 114. In accordance with embodiments of the present system, the memory 108 may include a transmission medium.

The MRR 102 may include a medical information memory (MIM) of the system and may therefore include medical records (MRs) such as MR of one or more users (hereinafter patients of the sake of clarity unless the context indicates otherwise) and may be located in one or more locations which may be local and/or remote from each other. The MIM may include a distributed memory which may include medical records of one or more medical providers (such as doctors, hospitals, etc.,); health professionals (e.g., chiropractors, psychologists, acupuncturists, medical testing centers, etc.); insurance companies; medical organizations; national or private medical databases; private medical memories (e.g., medical records of a patient stored on a private memory of the patient); etc., which may individually and/or collectively form a MR of one or more users. Thus, the system 100 may query a plurality of MIMs to obtain MRs of one or more users. Accordingly, the MRR 102 may be queried (e.g., accessed) by, for example, the server 106, the USs 112-x, etc., to obtain MRs related to the query. For example, the system may determine whether any current test results of a user 191 are available and obtain these results from the MIM. The MRR 102 may further filter or otherwise restrict access to MRs in accordance with access rules so as to enforce privacy and/or confidentiality settings of the user and/or system 100. The MRR 102 may for example further include information related to medications which a user may be taking.

Selection, access and/or retrieval of medical records of a user is discussed in U.S. Patent No. 61/418,395 the contents of which are incorporated herein by reference.

The sensors 110 may include a plurality of sensors such as sensors 110-1 through 110-N (generally 110-x) which may sense and generate corresponding sensor information. For example, the sensors 100-x may include one or more medical devices which may provide information such as pulse rate sensors, blood pressure sensors, blood glucose level sensors, blood oxygen level sensors, pulse rate sensors, electrocardiograph (ECG or EKG) sensors, imaging sensors, temperature sensors, biometric sensors, fingerprint sensors, iris sensors, genetic sequencers (e.g., DNA testers, coder/decoders, etc.), sound sensors (e.g., a microphone, etc.), etc., which may sense information related to a patient and report corresponding information as raw (e.g., blood pressure=100 mm Hg) or processed (e.g., blood pressure high) sensor information. Thus, the sensor information may include information such as information related to a patient's anatomy, physiology, vital signs, image, positions (e.g., standing, holding hand, etc.), body motions (e.g., rubbing stomach), etc.), lifting right forearm, location, and/or other information related to the patient. This information may be referred to as body monitoring readings of a patient or and may be obtained, when, for example, the system tracks selected body parts (SBPs) of a patient as will be described below. The sensors 110-x may include wired and/or wireless sensors which may be located locally and/or remotely from each other.

In accordance with embodiments of the present system, the sensors 110-x may also include imaging devices such as cameras which may capture image and/or video information related to a patient such as via a wireless device (e.g., a wireless US 112-x, etc.) in two- or three-dimensions (2-D or 3-D, respectively). Accordingly, the sensors may determine whether a user's movement such as range of motion, gate, etc., is normal, needs attention, etc. The sensor information such as the image information or other biometric information of a patient may be processed to identify (ID) a patient, symptoms of a patient, a medical condition of a patient, etc. Methods to determine symptoms and/or medical conditions of a patient are discussed in U.S. Patent Application No. 61/388,515, the contents of which are incorporated herein by reference.

The USs 112-1 thorough 112-M (generally 112-x) may include any suitable communication device with which a user may interact with the system and/or which may transmit and/or receive information from one or more of the MRR 102, the schedule resources 104, the server 106, the memory 108, the sensors 110, the USs 112-x, and/or the therapy resources 118. The USs 112-x may include a user interface (UI) 113 (e.g., a rendered UI) with which a user may interact with the US 112-x and/or sensors such a microphone, a camera, etc. Accordingly, the USs 112-x may include devices such as, for example, telephony devices (e.g., mobile stations (MSs), cellular phones, smart phones, soft phones (e.g., Internet Protocol (IP) Phones), conventional phones, etc.), personal digital assistances (PDAs) such as, for example, PALM™, RIM™, iPhone™, iPod™ iPad™, and other similar types of devices, personal computers (PCs), notebooks, netbooks, computing pads, and/or other types of communication devices. Further, the USs 112-x may include medical devices (e.g., a medical imaging device, an EKG, a blood pressure monitor, etc.) which may include sensors 110-x and may report various information such as sensor information to the server 106 in raw and/or processed form. Moreover, the USs 112-x may include 2-D or 3-D displays which may render information generated by the AR system 100 such as a patients image, AR limbs, etc., for the convenience of the patient.

The schedule resources 104 may include schedule information related to the schedules 116-1 through 116-M (generally 116-x) of one or more providers of professional services (POPS) such as medical services (e.g., a doctor, a doctor's office, a hospital, a clinic, etc.) or other related services (e.g., a chiropractor's office, etc.) should the present system indicate that a follow-up appointment is required as discussed further herein. Moreover, the schedule resources may provide information related to an available treatment, therapy, test, resource, professional, etc., and may be accessed in real-time and be subject to access rules which may define privacy and/or access restrictions which may be set by the system and/or the corresponding POPS. Thus, server 106 may request a schedule 116-x for a corresponding POPS and/or resource availability on a certain date (e.g., Jan. 25, 2015) and may receive corresponding schedule information. The schedules 116-x may then be updated in accordance with one or more appointments determined by the scheduling system 100 and stored in a memory of the system such as the schedule resources 102 and/or the memory 108 for later use.

The therapy resources 118 may include information related to one or more therapies such as therapy information which may include activity information (AI) related to a therapy and/or therapy course and which may include information related to one or more augmented-reality (AR) activities (e.g., elbow extensions), AR anatomical features, and/or range-of-motion (ROM) information, etc., as will be discussed with reference to FIG. 2 below. The server 106 may access the therapy resources 118 to obtain desired information such as information related to a selected therapy (or therapy course).

Figure 2:
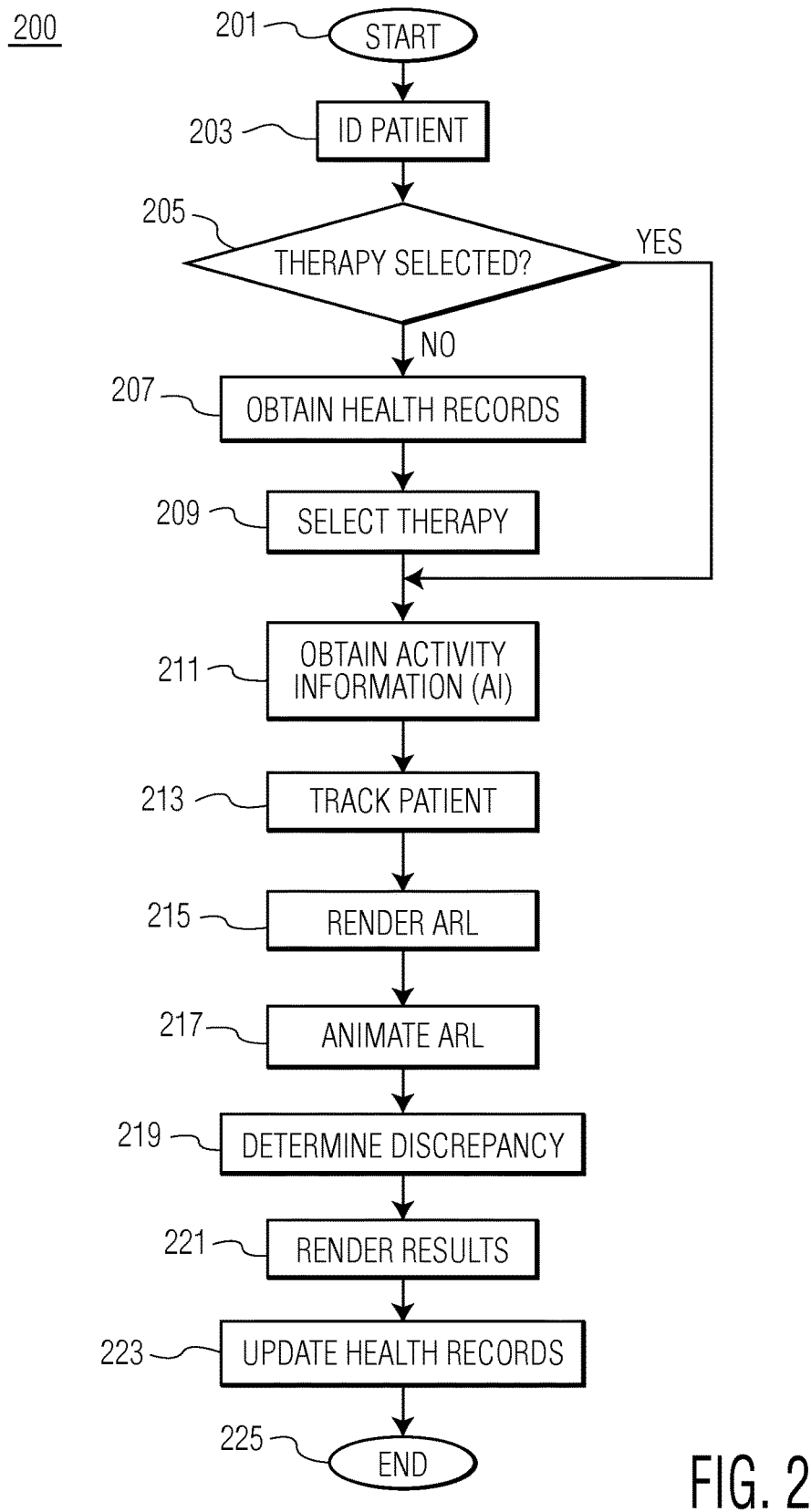
FIG. 2 shows a flow diagram that illustrates a process in accordance with embodiments of the present system.

FIG. 2 shows a flow diagram that illustrates a process 200 in accordance with embodiments of the present system. The process 200 may be performed using one or more computers communicating over a network such as the network 114. The process 200 can include one of more of the following acts. Further, one or more of these acts may be combined and/or separated into sub-acts, if desired. During process 200 a single user (e.g., a patient for the sake of clarity) may be discussed for the sake of clarity, however, the operative acts of the process 200 may be readily performed for a plurality of patients. In operation, the process 200 may start during act 201 and then proceed to act 203.

During act 203, the process may identify a patient using any suitable method. For example, the patient may be identified using biometric analysis of information related to the patient. Accordingly, the process may use any suitable biometric identification methods such as facial recognition (e.g., using a facial recognition application, etc.), fingerprint recognition, iris recognition, etc. to identify the patient. For example, to identify the patient using facial analysis, the process may obtain facial image information of the patient from an image capture device and perform facial recognition on the facial image information to identify the patient. However, it is also envisioned that a patient may be identified manually (e.g., entering identity (ID) information associated with a patient such as a name or social security number of the patient, scanning an identifier associated with the patient (e.g., an identity (ID) card, a therapy form, etc.), etc.). It is further envisioned that in other embodiments, the patient does not have to be identified or may remain anonymous, if desired. After completing act 203, the process may continue to act 205.

During act 205, the process may determine whether a therapy (e.g., including one or more courses which may also be identified with the therapy) has been selected for the patient (e.g., a selected therapy). The process may determine whether a therapy has been selected for the patient, by, for example, checking a suitable information source associated with the patient (e.g., a therapy information source) such as a therapy form (e.g., see, act 203 above), a user interface (UI) (e.g., information entered directly by a professional, etc.), etc., in order to determine whether a therapy has been selected for the patient. Accordingly, the process may obtain information related to one or selected therapies for the patient (e.g., rehabilitation of right hand performed once a week, for 20 weeks, currently in second course (e.g., second week), 18 courses remaining, etc.) from the therapy information source, if available.

Accordingly, if in accordance with embodiments of the present system, it is determined that a therapy for the patient has been selected, the process may continue to act 211. However, if it is determined that a therapy for the patient has not been selected, the process may continue to act 207.

During act 207, the process may obtain MR's of the patient from an MRR of the system, if available. Accordingly, the process may form a query to request information related to MCs of the patient (e.g., which may be filtered in accordance with current MCs, most recent MCs (e.g., last month, etc.), etc.) and may obtain corresponding information (e.g., related to MCs of the patient) from a memory of the system such as the MRR and obtain results of the query (or queries). After completing act 207, the process may continue to act 209.

During act 209, the process may select one or more therapies based upon the MC. For example, if the patient's MC indicates that the patients ACL is torn, the process may select an ACL related therapy (or therapy course) to be performed upon and/or by the patient. Further, when the therapy includes a plurality of courses, the process may determine (e.g., in response to historical information such as the MRs stored in a memory of the system) which course or courses of the plurality of courses to perform. For example, if process may determines that the patient tore his/her ACL last week, the process may select a first therapy course, while if the process determines that the patient tore his/her ACL two months ago, the process may select a different therapy course. Further, the process may determine progress that the patient is making during therapy and prescribe a therapy or therapy course based upon progress which the patient is determined to be making and may be obtained using information stored in, for example, the MRR such as the MRs. After completing act 209, the process may continue to act 211.

During act 211, the process may obtain activity information (AI) related to the selected therapy and/or therapy course and which may include information related to one or more augmented-reality (AR) activities (e.g., elbow extensions), AR anatomical features, and/or range-of-motion (ROM) information. The one or more AR anatomical features may correspond with selected body parts (SBPs) of the patient and may have a corresponding range-of-motion as defined by the ROM information. The information related to the AR anatomical features may further include information which may be processed to render one or more AR limbs (ARLs) which may correspond with one or more SBPs of the patient. Furthermore the process may determine a relationship between the one or more ARLs (e.g., a forearm ARL is connected to an arm ARL via an elbow). The ROM information may include information indicative of an expected ROM (FROM) which may be determined in accordance with various factors related to the patient such as anatomic factors, physiologic factors, an/or other information (e.g., therapy history information) which the process may use to adjust the ROM so as to form the FROM which may be unique to a patient. For example, to determine the FROM for a patient, the process may adjust a "default ROM" in accordance with information related to the patient such as height, anatomic dimensions (e.g., length of arm, forearm, hand, wrist, elbow, etc.), weight, body mass, age, MCs, medical procedures or operations (e.g., right elbow implant), etc., which may affect a patient's movement of the SBPs and thereby, form the FROM accordingly. The FROM may further include speed information which may used to determine whether a patient may be expected to move one or more body parts such as the SPBs at an expected speed (e.g., the patient should be able to lift his/her hand from a vertical position to a horizontal position in 0.75 seconds). The FROM and/or the speed information, may be calculated (e.g., by interpolation etc.) in real-time or obtained from a memory of the system. For example, the ROM may be obtained from a memory of the system such as a look up table wherein the ROM may be indexed in accordance with sex (e.g., Male), age, height, etc.), then the process may refine the ROM to determine the FROM in accordance with other physiologic or anatomic factors related to the patient such as medical history (e.g., broken elbow, etc.), body mass (muscular, regular, etc.), etc. After completing act 211, the process may continue to act 213.

During act 213, the process may track the patient. Accordingly, the process may obtain image information and process this information to track the patient in real time. For example, in accordance with embodiments of the present system, the process may obtain an image sequence (e.g., a plurality of image frames such as a video sequence, etc.) of the user in two- and/or three-dimensions (2-D or 3-D, respectively) and may process this information (e.g., using an image recognition application, etc.) to determine locations of one or more body parts of the user and/or orientation information such as an orientation of a user (e.g., facing 30 degrees to left, etc.,) using any suitable coordinate system, etc. Further, the process may determine a location of one or more parts of the patient's body which correspond with the one or more selected anatomical feature(s) of the patient such as the right forearm and elbow in the current example.

In accordance with embodiments of the present system, suitable image recognition applications may include 2-D Image recognition techniques such as ones using Haar Cascades, OpenCV, and other recognition technologies and/or 3-D Image recognition techniques using 2-D recognition combined with depth sensing (e.g., using "stereoscopy", "time of flight", "structured light", and other techniques).

In accordance with embodiments of the present system, an image recognition application may return one or more of the following data for further processing:
 1. Skeletal data including coordinates of the patient's joints and body parts
 2. A 3-D body map containing all the points where the patient is occupying space at any given time interval;
 3. Color information about the patient and immediate surroundings; and/or
 4. Other objects and their coordinates in the patient's immediate surroundings In accordance with embodiments of the present system, the location and/or orientation of a user's body parts may be determined using the information available for example though OpenNI/Kinect. In these embodiments, OpenNI/Kinect may send information on where various joints of the user are located in 3-D space. From this joint information, the orientation between joints may be calculated. For example, given the shoulder and elbow joints, the line formed between those two joints may be calculated. Thereafter, the angle of the line may be measured, for example oriented away from a predetermined reference orientation. For example, with this technique, the patient's rotator cuff angle may be calculated.

In any event, thereafter the process may track the one or more body parts (or selected body parts) of the patient and/or their locations in real time. After completing act 213, the process may continue to act 215. In the present example, it will be assumed that a present therapy defines selected body parts (SBPs) of the patient such as right hand, arm, elbow, and shoulder of the patient. Further, the process may include intelligent image recognition which may recognize (e.g., using information obtained from the MRs of the patient, image recognition, etc.) prosthetic devices (e.g., prosthetic limbs, etc.), deformities (e.g., right leg amputated below knee, etc.), etc.

During act 215, the process may render the ARLs superposed upon corresponding body parts (such as the SBPs) of the patient such as the right hand, forearm, elbow, arm, and shoulder in the current example. Accordingly, the process may form AR anatomical features such as one or more ARLs which correspond with the SBPs of the user. In order to construct one or more ARL, the present system may:
 looks at the person with a depth perception camera and identifies a person's limbs including length, width, and thickness of the limbs,
 for the target limb, approximates size and shape of limb based on above metrics,
 generates a computerized picture of the limb, namely the ARL, and superimposes this ARL in the same place in the video as where the person's limb, i.e. the corresponding body part, is initially located,
 the ARL will contain several pivot joints corresponding to the person's actual physical joints. The ARL can pivot on those joints to correspond with the exercise path that the patient is following.

The process may then integrate the ARLs with a real-time image sequence (e.g., a video sequence of the patient obtained using an image capture device such as a camera of the system) of the patient. The process may superimpose the ARLs upon an image (e.g., a real time image) of the patient so that the ARLs appear attached to the patient (if desired), and may maintain a relative position of the ARLs in relation to the corresponding selected body parts as the patient moves (if desired). Accordingly, the process may scale ARLs to correspond with the shape and/or size of the selected body parts of the patient and partially, or fully superimpose, scaled ARLs features upon the SBPs of the patient in real time.

Figure 3A:
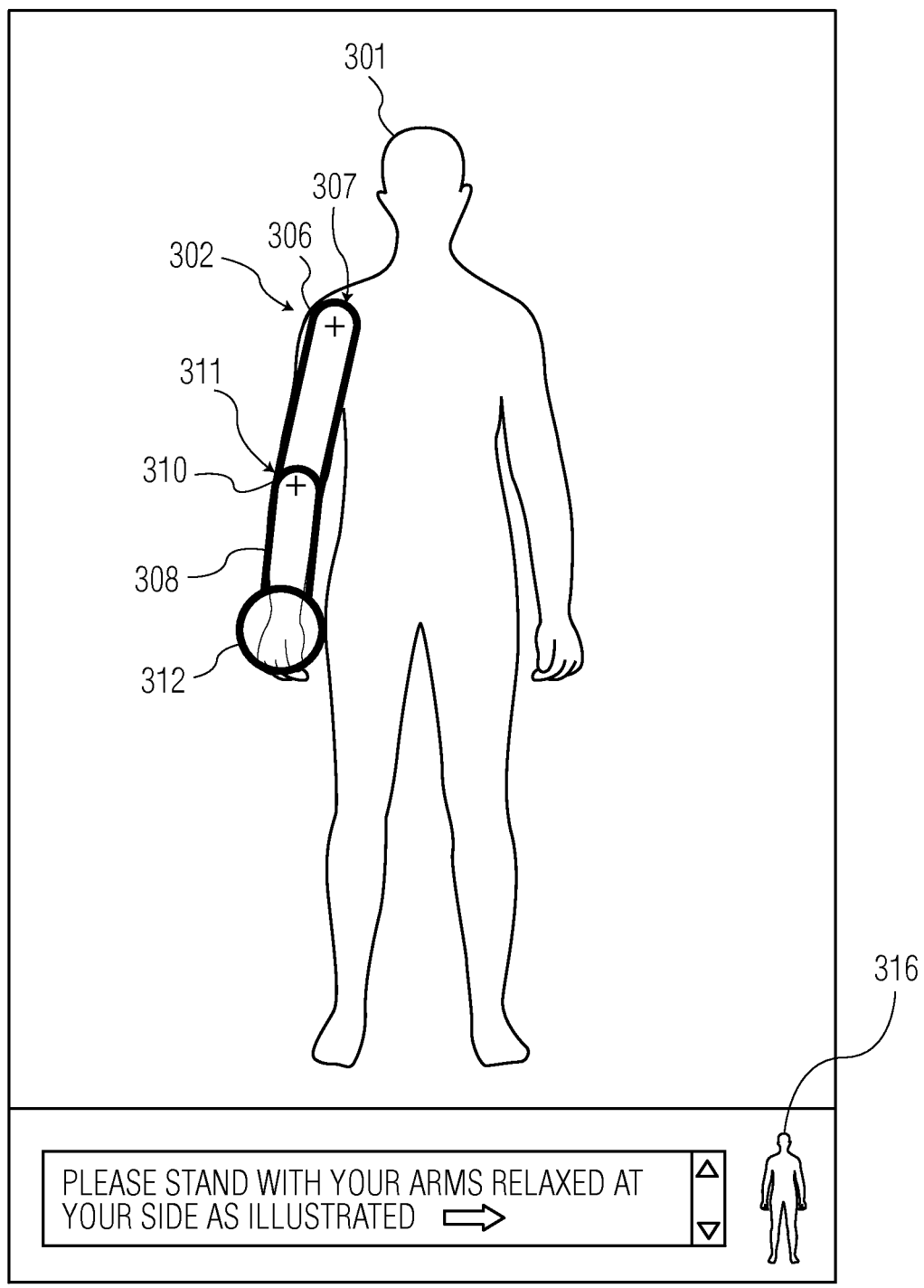
FIG. 3A is a screen shot which illustrates augmented-reality limbs (ARLs) superposed upon corresponding SBPs of a patient in accordance with embodiments of the present system.

FIG. 3A is a screen shot 300 which illustrates ARLs 302 superposed upon corresponding SBPs of a patient 301 in accordance with embodiments of the present system. In the present example, the ARLs generally 302 may include an arm ARL 306, a forearm ARL 308, a shoulder 307 an elbow ARL 310 and a hand ARL 312. The process may further determine approximate joint location (AJL) of one or more joints such as joints associated with the SBPs such as the elbow 311 and the shoulder 307 such as provided by the joint data returned directly by OpenNI/Kinect as discussed above. The process may superimpose the ARLs 302 such as the elbow ARL 310 upon an expected location of the corresponding AJL in an image of the patient which is rendered on a UI such as a display of the system. The process may track the patient in real-time and update the superposition of one or more of the ARLs 302 accordingly. In accordance with embodiments of the present system, the location of the augmented reality joints may be determined using a technique known as "forward kinematics". In accordance with these embodiments, a developer may supply a set of joint angles which describe a pose (e.g., supplied via JavaScript.). The present system may thereafter interpolate through those angles to create an animation leading into an updated position. Thus in accordance with embodiments of the present system as the patient moves, the superposition of the ARLs 302 may move accordingly.

Further, the process may track movement of the patient and/or the ARLs 302 over time and store this information for later use in a memory of the system. Further, instructions to the patient may be provided using audio information and/or visual information such as shown in information box 314 and/or a recommended body position 316 which may be generated by the process in accordance with the selected therapy (or course thereof). After completing act 215, the process may continue to act 217. During act 217, the patient may be told to remain in a relaxed position and/or the process may render ARLs of a preferred position. Accordingly, the process may inform the user using instructions such as, for example, "please stand with your arms resting at your side as illustrated," "please assume a resting position with your hands at your hips," "please remain in current position," etc., which may be rendered using any suitable method such as an audio and/or visual output (e.g. a speaker and a display, respectively).

During act 217, the process may animate the ARL in accordance with the expected ROM information. Accordingly, the ARL animations may be adjusted based upon calculated physiologic features of the patient (such as body weight and muscle mass which may affect the patient's ROM. For example, in accordance with embodiments of the present system, an algorithm such as edge detection algorithm may be utilized with the depth data of the user to isolate each limb. Thereafter, a 3-D collision area for each limb may be determined. In this way, the present system may calculate for example at what angle a limb would collide with the body. Accordingly, the process may move the ARLs to a desired position such as a position which may correspond with, for example, a desired position within an envelope of the FROM.

Figure 3B:
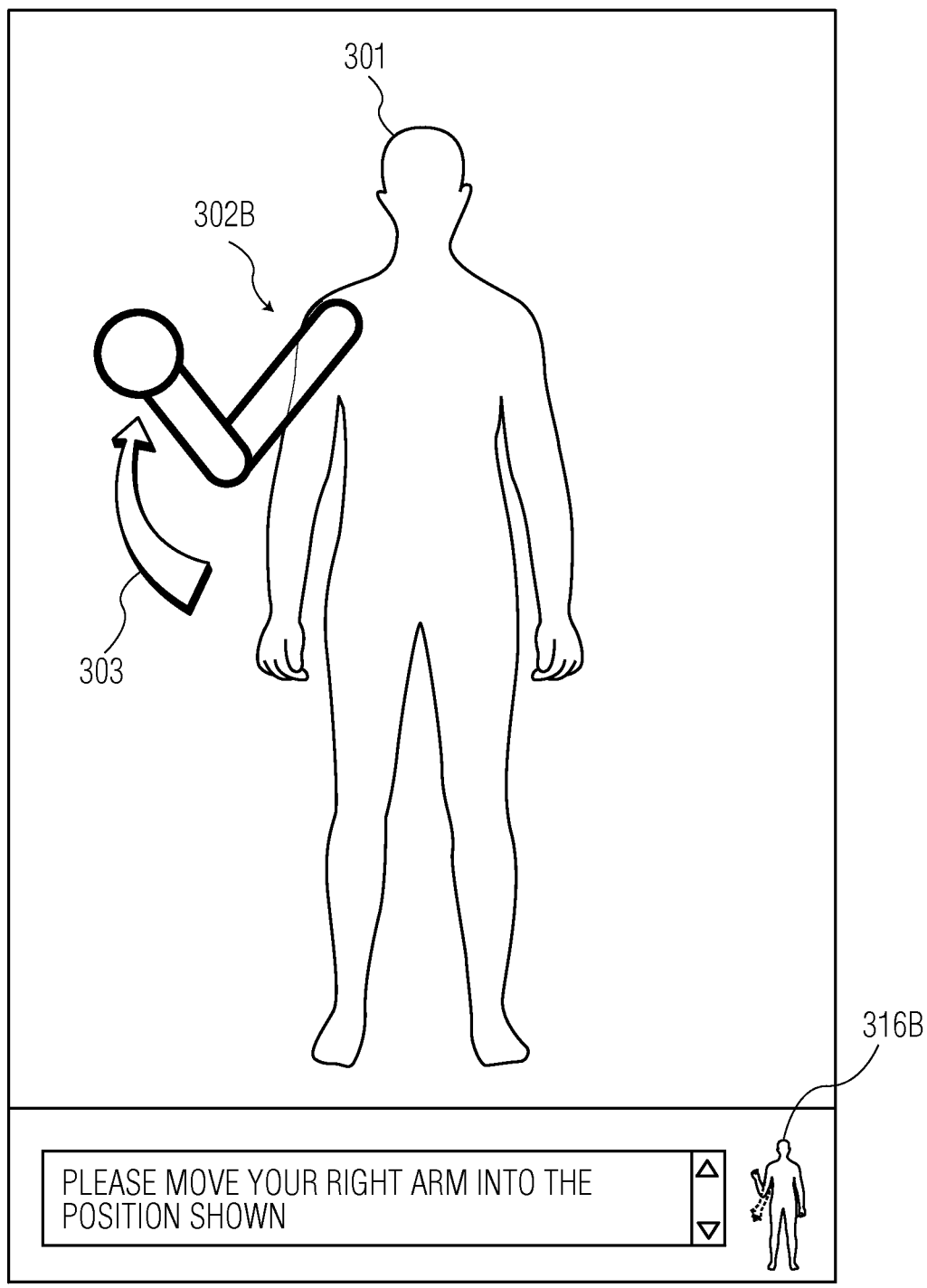
FIG. 3B is a screen shot which illustrates the ARLs corresponding with a desired position in accordance with an envelope of the FROM and partially superimposed upon corresponding body parts of the patient in accordance with embodiments of the present system.

FIG. 3B which is a screen shot 300B which illustrates the ARLs 302B corresponding with a desired position in accordance with an envelope of the FROM and partially superposed upon corresponding body parts of the patient 301 in accordance with embodiments of the present system. In the present example, the desired position may correspond with a maximum of the FROM as is illustrated by ARLs 302B of FIG. 3B. The process may further render an indication of a desired direction of movement from a current position of the SBPs of the patient 301 to the desired position as illustratively shown by ARLs 302B, arrow 303, and/or the recommended body position 316B. After completing act 217, the process may continue to act 219.

Figure 3C:
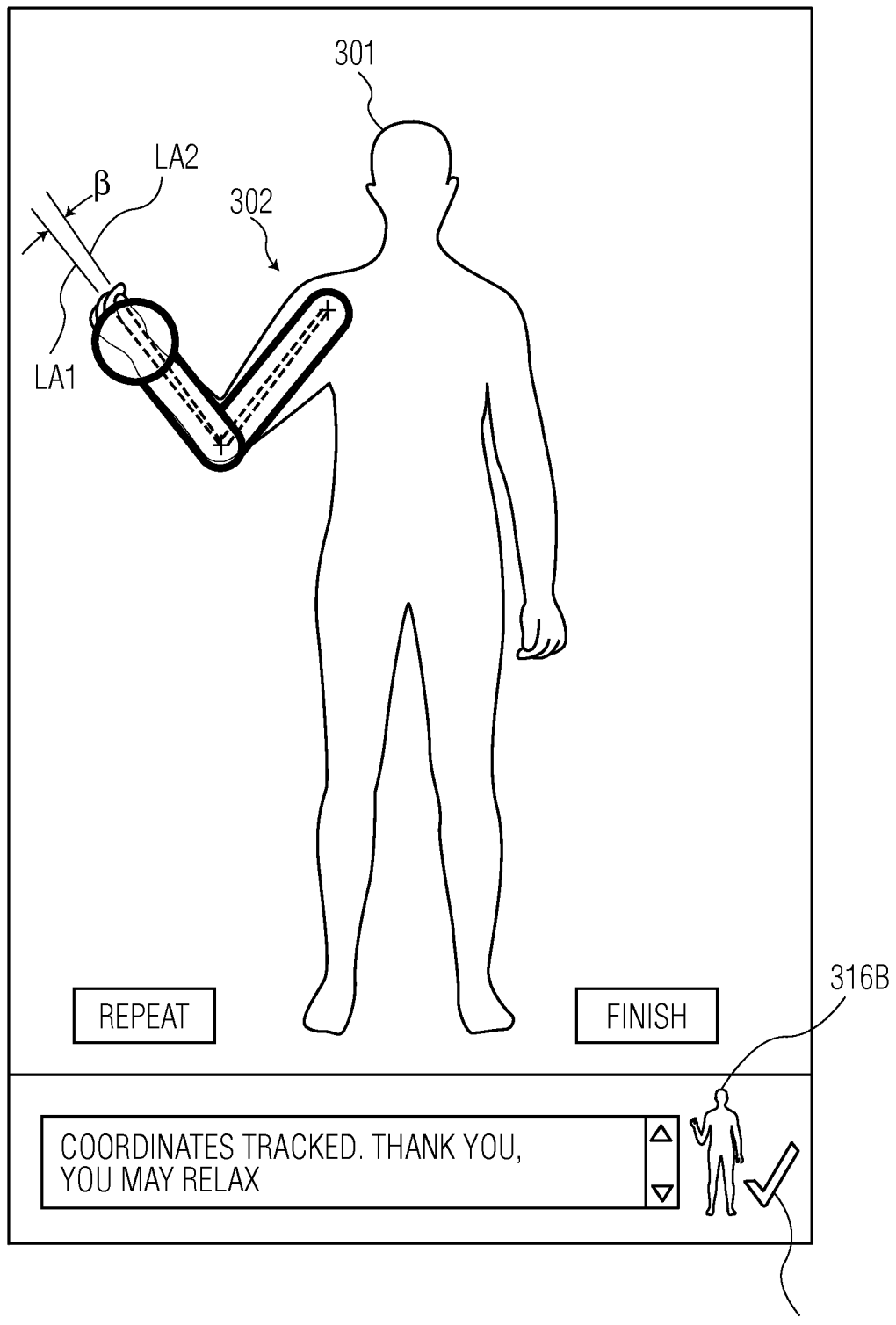
FIG. 3C is a screen shot illustrating the patient attempting to assume the desired ARL position illustrated by the ARLs of FIG. 3B.

During act 219, the process may determine a discrepancy in location between the patient's actual extension of the SBPs (e.g., the patient's forearm and arm in the present example) and the desired ARL position (e.g., of act 217 corresponding with the envelope of the FROM or another desired position (or positions) as illustrated in FIG. 3C which is a screen shot illustrating the patient 301 attempting to assume the desired ARL position illustrated by the ARLs 302B of FIG. 3B. Accordingly, the process may track the actual movement of SPBs of the patient and determine discrepancy between the actual position of the SBPs relative to the position of the corresponding ARLs using any suitable coordinate system. For example, in the present embodiment, a discrepancy in angular elbow joint movement is desired as set forth by the AI. This discrepancy may be represented by angle ($\beta$) and may be calculated using any suitable method. For example, the process may determine a first axis (LA1) which corresponds with an axis of a corresponding SBP such as a longitudinal axis the patient's forearm and a second axis (LA2) which corresponds with a longitudinal axis of a corresponding ARL (e.g., the forearm ARL). Then, the process may determine a point of intersection of the first and second axes which may correspond with a location of a corresponding AJL such as the elbow ARL 310 as determined by the process. The process may further determine an angle of $\beta$ which may originate at the AJL and may be defined by the first and second axes. Thus, the process may determine difference between an actual angle of the patient's elbow relative to desired location and/or angle of the elbow as defined by the ARL corresponding with the elbow.

Similarly, the process may determine discrepancies between positions of ARLs and actual movement of corresponding parts of the patient's body. In the present example, the process may compare the discrepancy (e.g., $\beta$ in the current example) with a corresponding threshold value (e.g., $\beta'$) to determine whether the discrepancy is greater than the corresponding threshold value. Accordingly, if it is determined that the discrepancy is greater than the corresponding threshold value, the process may set a flag which may indicate for example suboptimal movement. While, if it is determined that the discrepancy is less than or equal to the corresponding threshold value, the process may set a flag which may indicate for example optimal movement. Further, when determining FROM, the process may check this flag and set FROM accordingly. Moreover, the process may render information for the convenience of the user such as any determined discrepancies (e.g., $\beta$) and whether corresponding discrepancies are within (e.g., less than or equal to) corresponding threshold values. For example, in the present example, assuming that $\beta$ is within the threshold value $\beta'$, the process may render a graphic indicator such as a check mark 320 to inform the patient of results of the determination. Conversely, if the results of the determination exceed that threshold value, an "x" may be shown to indicate such. In accordance with embodiments of the present system, a range of movement that exceeds a further threshold may be detected similar as discussed above and indicated as exceptional movement.

Further, the process may provide instructions to the patient in real time such as to information the patient to take certain actions (e.g., "to hold your position," "extend further" (e.g., try to get closer to FROM), "change your position," "you may relax," etc. After completing act 219, the process may continue to act 221. However, if desired the process may repeat acts 215 through 219 as many times as desired and/or may adjust the FROM in accordance with a patient's determined abilities with each iteration of acts 219 through 221. The process may further provide a menu to a patient or other user (e.g., a professional) to access information and/or select various information such as whether the patient wishes to start, stop, continue, repeat, schedule an appointment with a professional, input information with respect to how the patient feels (e.g., "elbow pain at maximum extension"), etc., and may act in accordance with the input information. For example, upon determining that the patient experiences pain during the therapy (e.g., due to the therapy), the process may adjust the FROM to account for the experienced pain such as by reducing the illustrated ROM to alleviate the pain during the therapy.

During act 221, the process may render results of the determination using a UI of the system such as the display. For example, in the current example, the process may indicate that the patient's ROM is within expected ranges. However, it is also envisioned that the process may render results which may indicate that a patient's ROM exceeds or falls short of the FROM as discussed herein. Moreover, the process may determine a patient's progress, and render corresponding results for the convenience of the patient and/or a POPs. Further, it is envisioned that if the process may schedule the patient to have an appointment for services related to the therapy session such as an appointment with a professional (e.g., a doctor, etc.) should a doctor for example need to examine the patient due to an inability to achieve the FROM repeatedly. Accordingly, when, for example, the process determines that the patient's actual ROM is not within expected ranges or that the patient has not been making progress in the therapy sessions (e.g., as a result of a determination of a current therapy session with one or more previous therapy sessions, etc.), the process may determine (e.g., update) a treatment course for the patient and may schedule the patient to visit a provider of professional services in accordance with the selected treatment course. After completing act 221, the process may continue to act 223 where the process may update MRs corresponding with the patient in accordance with the results of the process and/or may update schedule information related to the patient. Then, the process may continue to act 225, where it illustratively ends.

Figure 4:
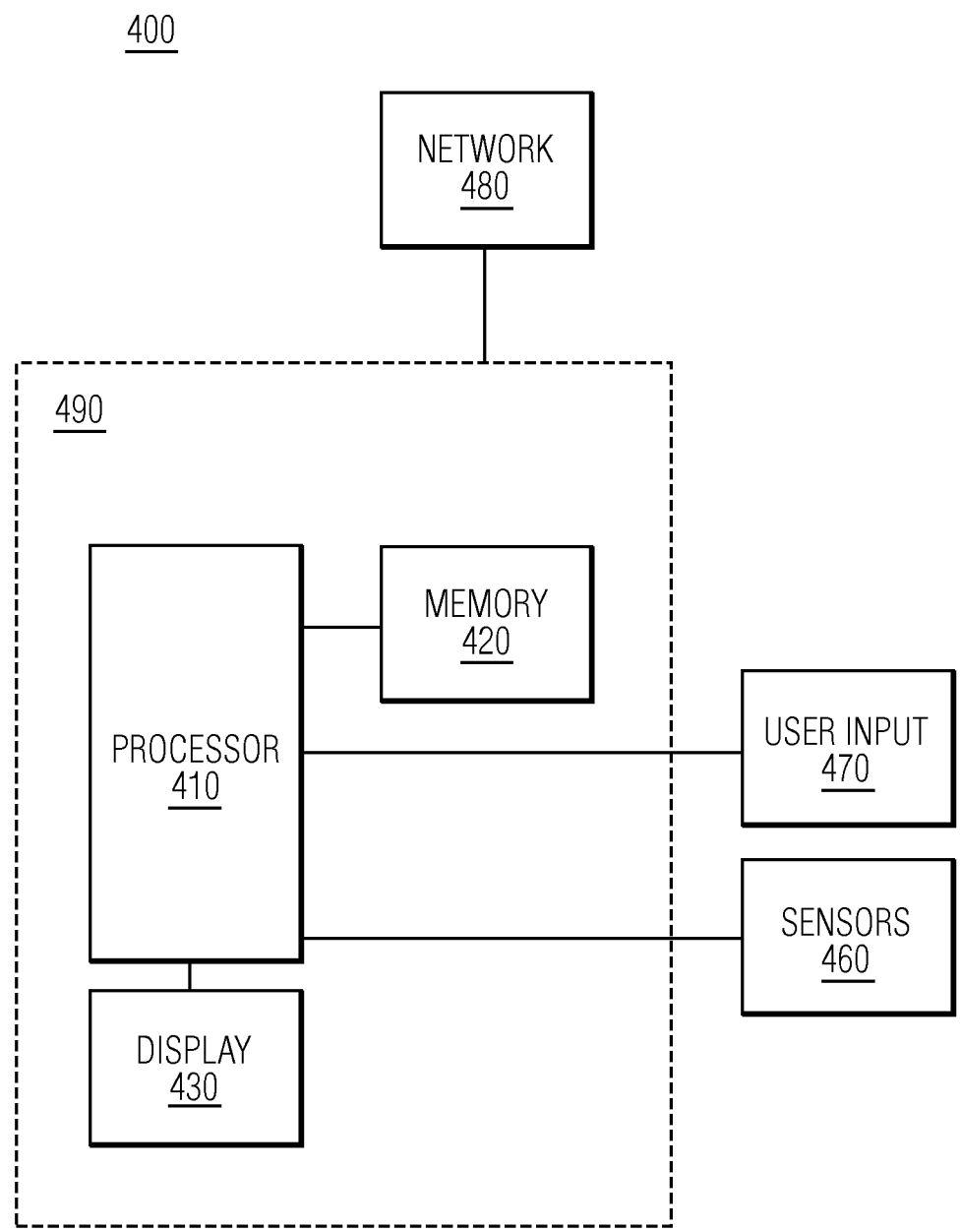
FIG. 4 shows a portion of a system in accordance with embodiments of the present system.

FIG. 4 shows a portion of a system 400 (e.g., control portion, retrieval portion, object recognition portion, image capture portion, US, etc.) in accordance with embodiments of the present system. For example, a portion of the present system may include a processor 410 operationally coupled to a memory 420, a display 430, a sensors 460, and a user input portion 470. The sensors 460 may include any suitable sensors such as imaging sensors such as one or more cameras, video cameras, x-ray, computed tomography (CT scan), sonogram, and/or other imaging scanners, etc., which may provide one or more images (e.g., a sequence of images, etc.) of one or more patients in two- and/or three-dimensions. Further, the sensors may include other sensors such as medical sensors which may provide feedback related to a patient's vitals or other physiological condition(s) such as pulse rate, breathing rates, blood pressure, body electrical activity (e.g., EKG) etc. These sensors may provide sensor information which may be analyzed by the system to determine a patient's medical status (exertion levels, blood pressure, medical symptoms or conditions, etc.), actual ROM, etc. The memory 420 may be any type of device (e.g., transitory and/or non-transitory) for storing application data as well as other data related to the described operation. The application data and other data are received by the processor 410 for configuring (e.g., programming) the processor 410 to perform operation acts in accordance with the present system. The processor 410 so configured becomes a special purpose machine particularly suited for performing in accordance with the present system.

The operation acts may include requesting, providing, and/or rendering of a patient's MR or therapy session related information (e.g., body movement, etc.) or filtered portions thereof. The user input portion 470 may include a keyboard, mouse, trackball or other device, including touch sensitive displays, which may be stand alone and/or be a part of a system, such as part of a personal computer, personal digital assistant (PDA), mobile phone, smart phone, set top box, television or other device for communicating with the processor 410 via any operable link. The user input portion 470 may be operable for interacting with the processor 410 including enabling interaction within a UI as described herein. Clearly the processor 410, the memory 420, display 430 and/or user input device 470 may all or partly be a portion of a computer system or other device such as a US and/or server as described herein.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 420 or other memory coupled to the processor 410.

The program and/or program portions contained in the memory 420 configure the processor 410 to implement the methods, operational acts, and functions disclosed herein. The memories may be distributed, for example between the clients and/or servers, or local, and the processor 410, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 410. With this definition, information accessible through a network is still within the memory, for instance, because the processor 410 may retrieve the information from the network for operation in accordance with the present system.

The processor 410 is operable for providing control signals and/or performing operations in response to input signals from the user input portion 470, the image capture portion 460, as well as in response to other devices of a network and executing instructions stored in the memory 420. The processor 410 may be an application-specific or general-use integrated circuit(s). Further, the processor 410 may be a dedicated processor for performing in accordance with the present system or may be a general-purpose processor wherein only one of many functions operates for performing in accordance with the present system. The processor 410 may operate utilizing a program portion, multiple program segments, and/or may be a hardware device utilizing a dedicated or multi-purpose integrated circuit.

Thus, in accordance with an embodiment of the present system, an augmented-reality limb (ARL) may be integrated with images such as live video of a patient. The ARL may be positioned so as to appear attached to the patient, and may maintain its position relative to the patient as the patient moves around or changes poses. Embodiments of the present system may be used to enhance rehabilitation tests and/or procedures such as a joint rehabilitation procedure. For example, an ARL may be rendered to illustrate a motion which may be used to test a particular degree of freedom of a joint, and the patient may be requested to attempt to obtain an illustrated ROM using a corresponding body part. The system may track the movement of the patient, may determine discrepancy in motion. Then results of the determination may be rendered for the convenience of the user and/or stored for later use.

It is further envisioned that the embodiments of the present system may measure the extent to which the patient is able to replicate motions corresponding with a range-of-motion determined by the system. Moreover, the system may determine whether any improvement in the patient's mobility is made between tests. Further, the system may include software applications which may be designed to allow for any portion of the body to be selected as a selected body part and the system may generate corresponding ARLs to animate the selected body parts. Further, it is envisioned that embodiments of the present system may provide ARL animations whose motion may be adjusted in accordance with calculated features of the patient such as body height, weight, muscle mass, etc., which may affect the patient's ROM. Moreover, it is envisioned that if a patient has a prosthetic limb with an active control system (e.g., a digital control system, etc.) the system may detect impulses or other control mechanisms and determine and render (e.g., in real time) corresponding movement of the prosthetic limb (e.g., without the limb attached to the patient). It is further envisioned that embodiments of the present system may render instructional body motions which may be provided to teach a patient a proper stance for a martial arts move, yoga training, etc. Moreover, it is envisioned that embodiments of the present system may render additional limbs (e.g., two sets of arms, forearms, etc.,) superimposed upon a patient's body for video gaming etc.

With respect to physical therapy, embodiments of the present system may provide an AR method to monitor a ROM of a user's limb such as a patient's arm, leg, elbow, etc. Accordingly, a patient may measure progress when receiving therapy using embodiments of the present system by, for example, visually observing the patient's ROM as opposed to a ROM of normal limb or the FROM. Generally, embodiments of the present system may provide a general method where a motion may be rendered to a patient and thereafter the system may capture the motion. The, the system may determine an FROM in accordance with information store in a memory of the system such as a range-of-motion database which may include normal expected range-of-motions in accordance with information related to a patient's physiology such as height, weight, age, muscle mass, medical conditions, etc. Further, the system may obtain MR of a patient such as PHRs and may determine FROM of the patient in accordance with the MR information such as length of limbs, size/width of torso, position of hips, etc. Further, the system may adjust the FROM in accordance with information obtained from the MR. For example, if the MR indicates that the patient has a bad hip, then, the system may adjust the FROM in accordance with this information and may limit the FROM for the bad hip. In accordance with embodiments of the present system, the FROM for a patient may be stored for later use when, for example, setting a newer FROM, for determining progress of therapy courses, etc. Thus, the system may determine a normal range-of-motion based upon information obtained from a patient's MR (e.g., patient has limited movement of right hip due to hip replacement) and determined physiological characteristics of the patient such as length of limbs, size of torso, positions of hips, etc. (which may be determined using an image recognition system etc.). Then, the system may adapt a therapy or exercise accordingly and render motions of the therapy or exercise using AR techniques.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, the section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated; and i) the term "plurality of" an element includes two or more of the claimed element, and does not imply any particular range of number of elements; that is, a plurality of elements may be as few as two elements, and may include an immeasurable number of elements.

What is claimed is:

1. A method of presenting augmented-reality limbs to a user, the method comprising acts which are performed by a processor, the method comprising acts of:

obtaining activity information (AI) comprising information related to one or more of augmented-reality (AR) activity information, AR anatomical feature information, or range-of-motion (ROM) information;

obtaining user information comprising information related to one or more of the anatomy or physiology of the user;

tracking selected body parts (SBPs) of the user corresponding with the AR anatomical feature information;

determining one or more augmented-reality limb (ARLs) corresponding to the tracked SBPs using the AI and the user information;

determining expected range of motion (EROM) information in accordance with the AI and the user information; and rendering the one or more ARLs on a display in relation with one or more tracked SBPs of the user, wherein the rendering comprises animating the one or more ARLs in accordance with one or more of the AR activity information or the EROM information.

2. The method of claim 1, wherein the one or more ARLs are further linked to a corresponding SBP of one or more of the SBPs of the user.

3. The method of claim 1, further comprising an act of determining an actual ROM of one or more of the tracked SPBs of the user.

4. The method of claim 3, further comprising an act of determining a discrepancy in range-of-motion based upon a comparison of the actual ROM of the one or more tracked SBPs of the user with the corresponding EROM information.

5. The method of claim 4, further comprising an act of determining whether the discrepancy is greater than a threshold ROM value and rendering results of the determination.

6. A server to present augmented reality limbs a user, the server comprising:

a display; and a processor which is configured to:

obtain activity information (AI) comprising information related to one or more of augmented-reality (AR) activity information, AR anatomical feature information, or range-of-motion (ROM) information;

obtain user information comprising information related to one or more of the anatomy or physiology of the user;

track selected body parts (SBPs) of the user corresponding with the AR anatomical feature information;
determine one or more augmented-reality limb (ARLs) corresponding to the tracked SBPs using the AI and the user information;
determining expected range of motion (EROM) information in accordance with the AI and the user information; and
render the one or more ARLs in relation with one or more tracked SBPs of the user on the display of the server, wherein the rendering comprises animating the one or more ARLs in accordance with one or more of the AR activity information or the EROM information.

7. The server of claim 6, wherein the processor is configured to link the one or more ARLs to a corresponding SBP of one or more of the SBPs of the user.

8. The server of claim 6, wherein the processor is configured to determine an actual ROM of one or more of the tracked SPBs of the user.

9. The server of claim 8, wherein the processor is further configured to determine a discrepancy in range-of-motion based upon a comparison of the actual ROM of the one or more tracked SBPs of the user with the corresponding EROM information.

10. The server of claim 9, wherein the processor is configured to determine whether the discrepancy is greater than a threshold ROM value and renders results of the determination.

11. A computer readable non-transitory memory medium comprising a computer program stored thereon, the computer program configured to perform a therapy process on a user when executed by a processor, the computer program comprising a program portion configured to implement a method of presenting augmented-reality limbs to a user, the method comprising acts which are performed by the processor:

obtaining activity information (AI) comprising information related to one or more of augmented-reality (AR) activity information, AR anatomical feature information, or range-of-motion (ROM) information;
obtaining user information comprising information related to one or more of the anatomy or physiology of the user;
tracking selected body parts (SBPs) of the user corresponding with the AR anatomical feature information;
determining one or more augmented-reality limb (ARLs) corresponding to the tracked SBPs using the AI and the user information;
determining expected range of motion (EROM) information in accordance with the AI and the user information; and
rendering the one or more ARLs on a display in relation with one or more tracked SBPs of the user, wherein the rendering comprises animating the one or more ARLs in accordance with one or more of the AR activity information or the EROM information.

* * * * *